United States Patent
Gami et al.

(10) Patent No.: US 8,350,109 B2
(45) Date of Patent: Jan. 8, 2013

(54) PRODUCTION OF STYRENE FROM ETHYLBENZENE USING AZEOTROPIC VAPORIZATION AND LOW OVERALL WATER TO ETHYLBENZENE RATIOS

(75) Inventors: Ajaykumar Chandravadan Gami, East Brunswick, NJ (US); Sanjeev Ram, Berkeley Heights, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 112 days.

(21) Appl. No.: 12/966,258

(22) Filed: Dec. 13, 2010

(65) Prior Publication Data
US 2012/0149960 A1    Jun. 14, 2012

(51) Int. Cl.
C07C 5/42    (2006.01)
(52) U.S. Cl. .................. 585/441; 585/435; 585/440
(58) Field of Classification Search .............. 585/440, 585/441, 252, 444
See application file for complete search history.

(56) References Cited

U.S. PATENT DOCUMENTS

| | | | |
|---|---|---|---|
| 4,615,769 | A | 10/1986 | Horigome et al. |
| 4,628,136 | A | 12/1986 | Sardina |
| 4,695,664 | A | 9/1987 | Whittle |
| 5,386,075 | A | 1/1995 | Keil et al. |
| 7,642,390 | B2 | 1/2010 | Oleksy et al. |
| 7,687,677 | B1 | 3/2010 | O'Brien et al. |
| 2005/0245779 | A1* | 11/2005 | Oleksy et al. ........... 585/444 |
| 2010/0111785 | A1 | 5/2010 | Oleksy et al. |
| 2010/0240940 | A1 | 9/2010 | Wilcox et al. |

OTHER PUBLICATIONS

J. D. Seader, Jeffrey J. Siirola, Scott D. Barnicki, "Perry's Chemical Engineer's Handbook," 1997, McGraw-Hill, Seventh edition, 13-4 to 13-9.*
International Search Report and Written Opinion issued May 30, 2012 in corresponding international application No. PCT/US2011/060974 (10 pages).

* cited by examiner

Primary Examiner — In Suk Bullock
Assistant Examiner — Candace R Chouinard
(74) Attorney, Agent, or Firm — Osha Liang LLP

(57) ABSTRACT

A process for dehydrogenation of alkylaromatic hydrocarbon, including: contacting a reactant vapor stream, comprising an alkylaromatic hydrocarbon and steam and having a first steam to alkylaromatic hydrocarbon ratio, with a dehydrogenation catalyst to form a vapor phase effluent comprising a product hydrocarbon, the steam, and unreacted alkylaromatic hydrocarbon; feeding at least a portion of the effluent to a splitter to separate the product hydrocarbon from the unreacted alkylaromatic hydrocarbon; recovered from the splitter as bottoms and overheads fractions, respectively; recovering heat from a first portion of said overheads fraction by indirect heat exchange with a mixture comprising alkylaromatic hydrocarbon and water to at least partially condense said portion and to form an azeotropic vaporization product comprising alkylaromatic vapor and steam having a second steam to alkylaromatic hydrocarbon ratio; and combining the azeotropic vaporization product with additional alkylaromatic hydrocarbon and additional steam, together or separately, to form the reactant vapor stream.

8 Claims, 4 Drawing Sheets

PRODUCTION OF STYRENE FROM ETHYLBENZENE USING AZEOTROPIC VAPORIZATION AND LOW OVERALL WATER TO ETHYLBENZENE RATIOS

FIELD OF THE DISCLOSURE

Embodiments disclosed herein relate to a process for the production of styrene by the dehydrogenation of ethylbenzene in the presence of steam. More particularly, embodiments disclosed herein relate to dehydrogenation of ethylbenzene at lower overall water to ethylbenzene weight ratios (lower overall water (steam) to oil weight ratios) when recovering heat of condensation of the various dehydrogenation products, such as ethylbenzene from styrene, via azeotropic vaporization of the liquid ethylbenzene and water feeds to the dehydrogenation reactor.

BACKGROUND

U.S. Pat. No. 4,628,136 (the '136 patent) teaches a method of recovering the heat contained in the overhead of the ethylbenzene/styrene monomer (EB/SM) splitter by using this stream to boil an azeotropic mixture of ethylbenzene and water, which, once vaporized, is subsequently transferred to the reaction system where dehydrogenation of ethylbenzene to styrene takes place. As described in the '136 patent, the EB feed is vaporized with water in the overhead of the EB/SM separation Column. This is possible as EB and water forms a low boiling point azeotrope.

Referring now to FIG. 1, a simplified process flow diagram for the azeotropic heat recovery similar to that as described in the '136 patent is illustrated. Crude styrene from the dehydrogenation reactor (or upstream separations) is fed via flow line 10 to the EB/SM splitter 12. Styrene product is recovered as a bottoms fraction 14, and ethylbenzene, possibly along with other impurities such as benzene, toluene, and xylenes (BTX), are recovered as an overheads fraction 16. The overheads fraction 16 is condensed via indirect heat exchange with ethylbenzene (recycle and/or fresh) and water (such as condensate recovered from the dehydrogenation product), fed via flow line 18, in azeotropic vaporizer 20. The condensed overhead fraction is recovered from azeotropic vaporizer 20 via flow line 22, a portion of which may be used for column reflux, and a portion of which may be fed to downstream processes (not shown), such as for the recovery of BTX when these components are not separated upstream of the EB/SM splitter. The vaporized azeotropic mixture of EB and water is recovered from azeotropic vaporizer 20 via flow line 24 for feed to the dehydrogenation reaction zone (not illustrated).

The weight ratio of EB and water vapor in stream 24 is commonly referred to as the Primary Steam to Oil weight ratio in the dehydrogenation reaction area. (PS/Oil weight ratio). This configuration, as described in the '136 patent, saves the energy associated with the boiling of EB and water as this mixture is vaporized against EB/SM Separation column overhead vapor, which would otherwise be condensed using cooling water.

Referring now to FIG. 2, a simplified flow diagram for a typical configuration for the dehydration reaction area is illustrated. SM is manufactured by dehydrogenating the EB feed, which is an endothermic reaction. The vaporized azeotropic mixture of EB and water is fed via flow line 24 to the reaction zone, which may include two to four dehydrogenation reactors 26, 28. The effluent from each reactor 26 may be reheated using steam before entering the next reactor 26 or final reactor 28. The steam used for reheating the reactor effluents is commonly referred to as Main Steam (MS), which is provided from a steam superheater 30 via flow line 32 and eventually enters at the inlet 34 of the first reactor 26 along with the PS/Oil (vaporized EB/water) mixture, which may also be preheated against the effluent from final reactor 28 in exchanger 36.

As noted in the background of the '136 patent, the focus in the industry may fluctuate periodically between energy efficiency and catalyst developments, among other concerns. However, improvements in these distinct areas may affect the overall process. For example, new catalysts are available, and others may be in development, which allow operation of the dehydrogenation reactor at lower overall steam to oil weight ratios ((MS+PS)/oil). For example, new catalysts being developed may allow for operation at an overall steam to oil weight ratio of 0.9 to 1.0, or even lower.

The azeotropic vaporization of the ethylbenzene-water mixture, at conditions suitable for cross-exchange with the overheads from the EB/SM splitter, provides only a limited variability in the control of the PS/Oil weight ratio of the vaporized azeotropic mixture. As a result, operation at lower overall steam to oil weight ratios would require a decrease in the amount of main steam (MS). However, decreasing the amount of main steam impacts the reheating of reactor effluents between the reaction stages. Thus, with a smaller amount of MS, higher furnace and transfer line temperatures are required as the same reaction heat needs to be provided (for equivalent SM production rates). However, at overall S/O weight ratios of 1.0 or lower, the temperatures needed to provide the required heat may exceed the current metallurgical limitations of the heater coils 38 as well as the associated transfer lines.

SUMMARY OF THE DISCLOSURE

It has been found that using only a portion of the EB/SM splitter overheads to provide heat to the azeotropic vaporizer may provide for realization of the full benefit of heat recovery from the EB/SM splitter overheads, as well as sufficient process flexibility so as to operate the dehydrogenation reaction zone over a wide range of overall steam to oil weight ratios, including overall steam to oil weight ratios of less than 1.0. The benefits of embodiments disclosed herein may be realized without reducing the Main Steam to Oil weight ratio, thus providing for the necessary reactor effluent reheat capacity.

In one aspect, embodiments disclosed herein relate to a process for the dehydrogenation of an alkylaromatic hydrocarbon, the process including: contacting a reactant vapor stream, comprising an alkylaromatic hydrocarbon and steam and having a first steam to alkylaromatic hydrocarbon weight ratio, with a dehydrogenation catalyst in a reaction zone comprising one or more reactors under dehydrogenation conditions so as to form a vapor phase effluent comprising a product hydrocarbon, the steam, and unreacted alkylaromatic hydrocarbon; feeding at least a portion of the effluent to a splitter to separate the product hydrocarbon from the unreacted alkylaromatic hydrocarbon; recovering the unreacted alkylaromatic hydrocarbon from the splitter as an overheads fraction; recovering the product hydrocarbon from the splitter as a bottoms fraction; recovering heat from a first portion of said overheads fraction by indirect heat exchange with a mixture comprising alkylaromatic hydrocarbon and water to at least partially condense said portion and to form an azeotropic vaporization product comprising alkylaromatic vapor and steam having a second steam to alkylaromatic hydrocarbon weight ratio; combining the azeotropic vaporization product with additional alkylaromatic hydrocarbon and additional steam, together or separately, to form the reactant vapor stream.

Other aspects and advantages will be apparent from the following description and the appended claims.

DETAILED DESCRIPTION

Embodiments disclosed herein relate to a process for the production of styrene by the dehydrogenation of ethylbenzene in the presence of steam. More particularly, embodiments disclosed herein relate to dehydrogenation of ethylbenzene at lower overall steam to ethylbenzene weight ratios (lower overall steam to oil weight ratios) while also recovering heat of condensation of the various dehydrogenation products, such as ethylbenzene from styrene, via azeotropic vaporization of the liquid ethylbenzene and water feeds to the dehydrogenation reactor.

Figure 3:
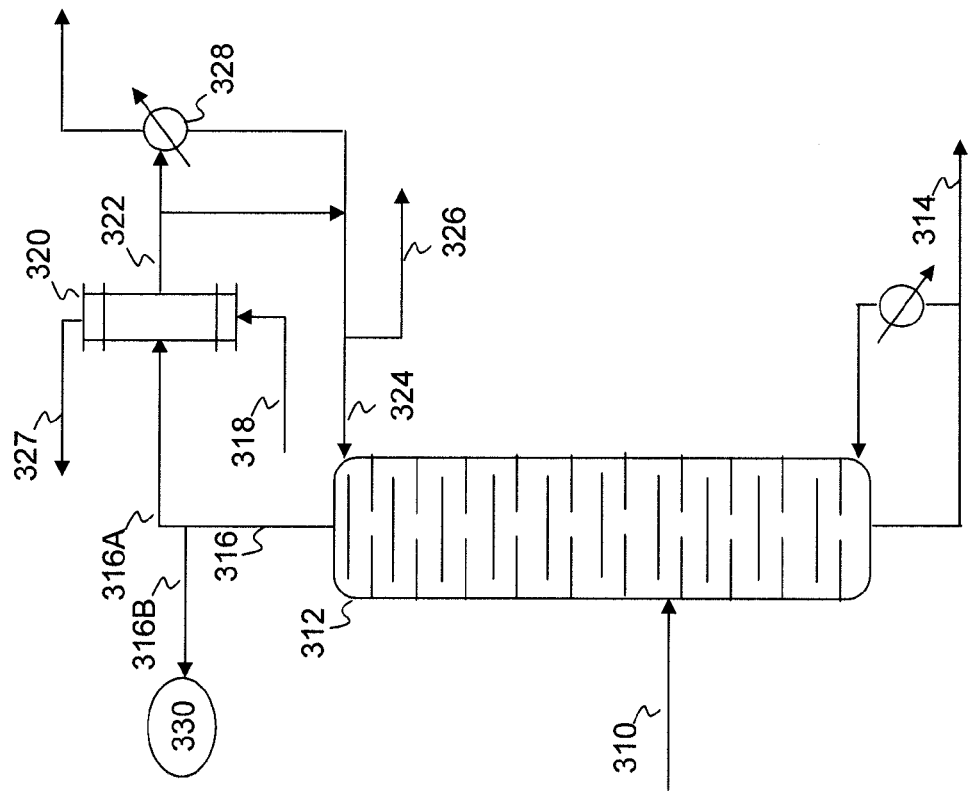
FIG. 3 is a simplified flow diagram of a portion of a process for the production of styrene monomer (SM) according to embodiments disclosed herein.
Figure 1:
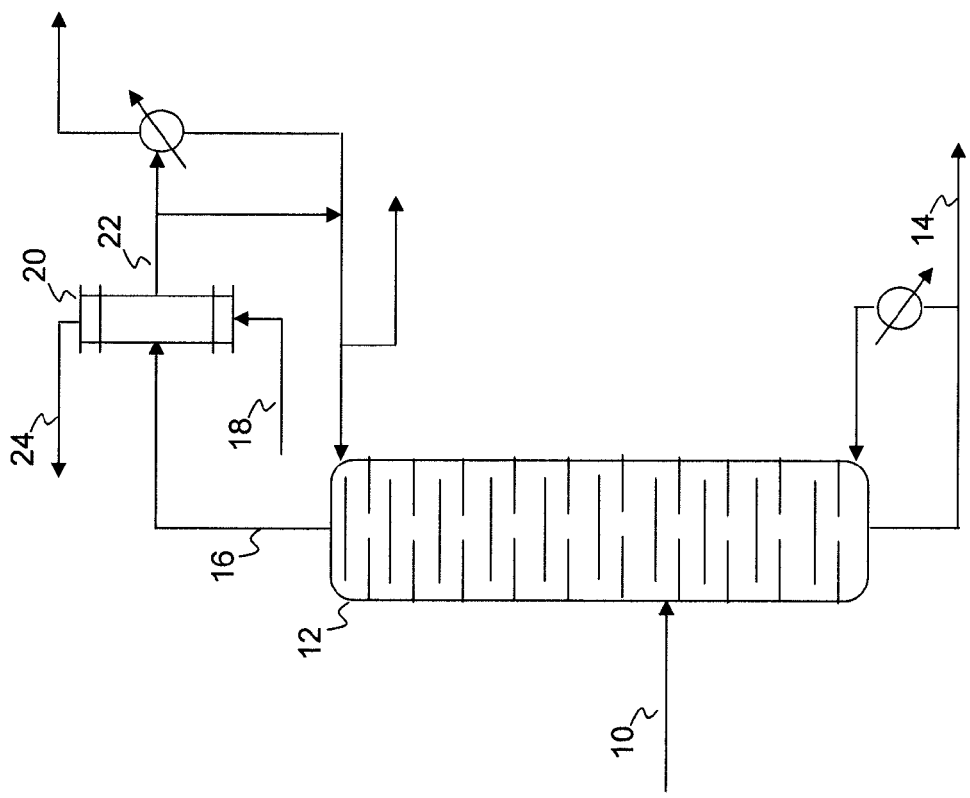
FIG. 1 is a simplified flow diagram of a prior art method for heat recovery from the overheads of an ethylbenzene/styrene monomer (EB/SM) splitter using an azeotropic vaporizer.

Referring now to FIG. 3, a simplified process flow diagram for heat recovery from the overheads of an ethylbenzene/styrene monomer (EB/SM) splitter using an azeotropic vaporizer according to embodiments disclosed herein is illustrated. Crude styrene recovered via flow line 310 from the dehydrogenation reaction zone and any intermediate separation zones (not illustrated) may be fed to EB/SM splitter 312 for separation of styrene and any heavy byproducts from unreacted ethylbenzene and any additional light components, such as benzene, toluene, and xylenes. The styrene product and heavies may be recovered from splitter 312 as a bottoms fraction 314, and the ethylbenzene and any light hydrocarbons may be recovered from splitter 312 as an overheads fraction 316. A portion 316A of the overheads fraction 316 is then condensed via indirect heat exchange with ethylbenzene (recycle and/or fresh) and water (such as condensate recovered from the dehydrogenation product), fed via flow line 318, in azeotropic vaporizer 320. The condensed overhead fraction is recovered from azeotropic vaporizer 320 via flow line 322, a portion of which may be used for column reflux 324, and a portion of which may be recovered as ethylbenzene recovery stream 326, which may be fed to downstream processes (not shown), such as for the recovery of BTX when these components are not separated upstream of the EB/SM splitter. The vaporized azeotropic mixture of EB and water is recovered from azeotropic vaporizer 320 via flow line 327 for feed to the dehydrogenation reaction zone (not illustrated). The remaining portion 316B of the overheads fraction 316 is not used to provide heat to azeotropic vaporizer 320.

Use of only a portion of the splitter overheads fraction to provide heat to the azeotropic vaporizer results in a there not being enough heat to vaporize the entire ethylbenzene and primary steam feed to the dehydrogenation reaction zone. A supplemental ethylbenzene feed may then be mixed with the azeotropic mixture recovered from the vaporizer to provide the additional ethylbenzene required to reach the total ethylbenzene feed rate desired. The lower vaporization rate in the azeotropic vaporizer results in a decrease in the primary steam, and when combined with the main steam, may provide for a lower overall steam to oil weight ratio entering the dehydrogenation reaction zone.

As noted above, it is undesirable to significantly decrease the amount of main steam, as this impacts the reheating of reactor effluents between the reaction stages and may result in excessive furnace and transfer line temperatures. By using only a portion of the splitter overheads fraction to provide heat to the azeotropic vaporizer, the overall steam to oil weight ratio may be adjusted while not decreasing the reheat steam provided from the steam superheater. Even if the flow rate of the steam from the steam superheater is decreased, using only a portion of the splitter overheads fraction to provide heat to the azeotropic vaporizer may allow operation at lower furnace and transfer line temperatures, within their respective metallurgical limitations.

Figure 2:
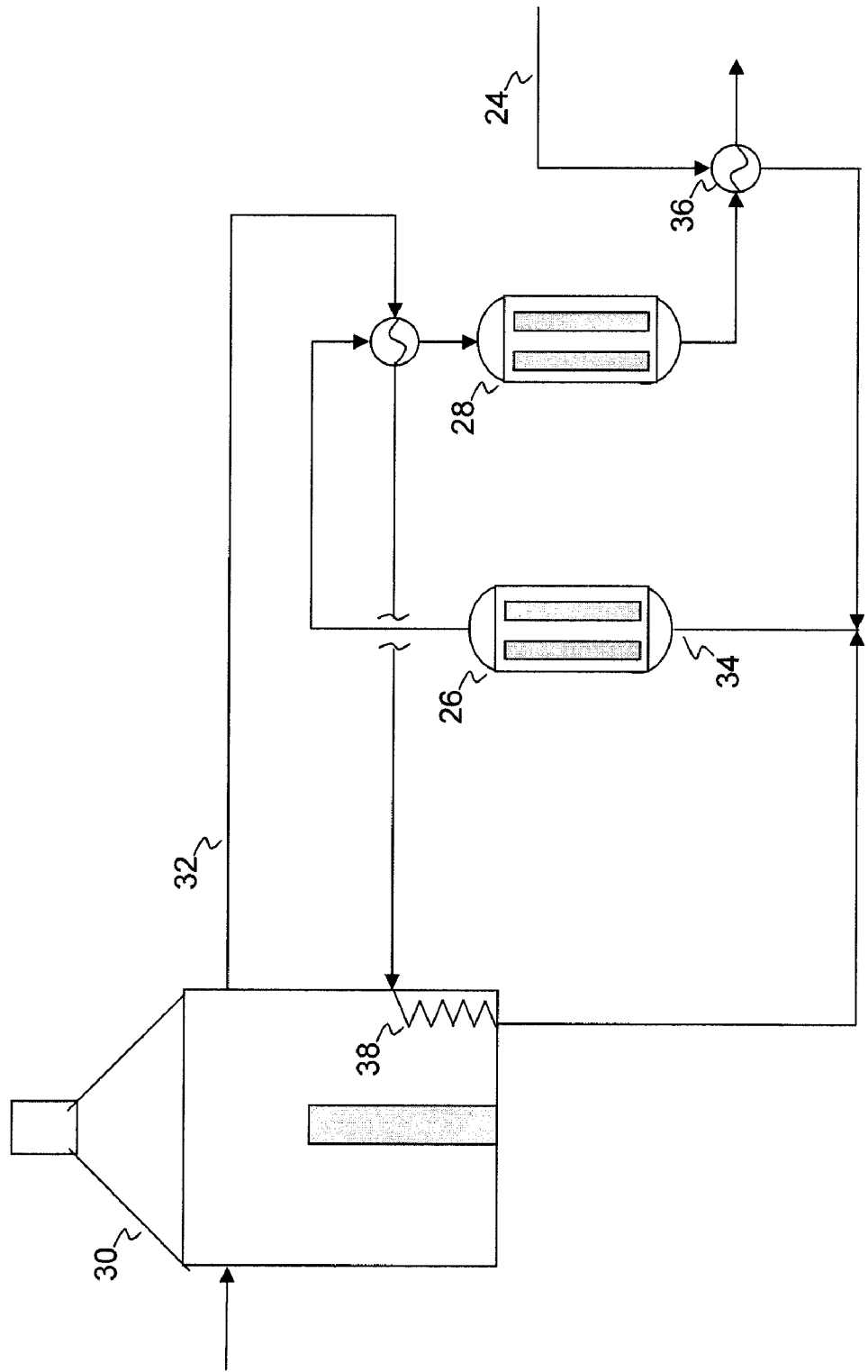
FIG. 2 is a simplified flow diagram of a typical dehydrogenation reaction system for the production of styrene monomer (SM) from ethylbenzene (EB).
Figure 4:
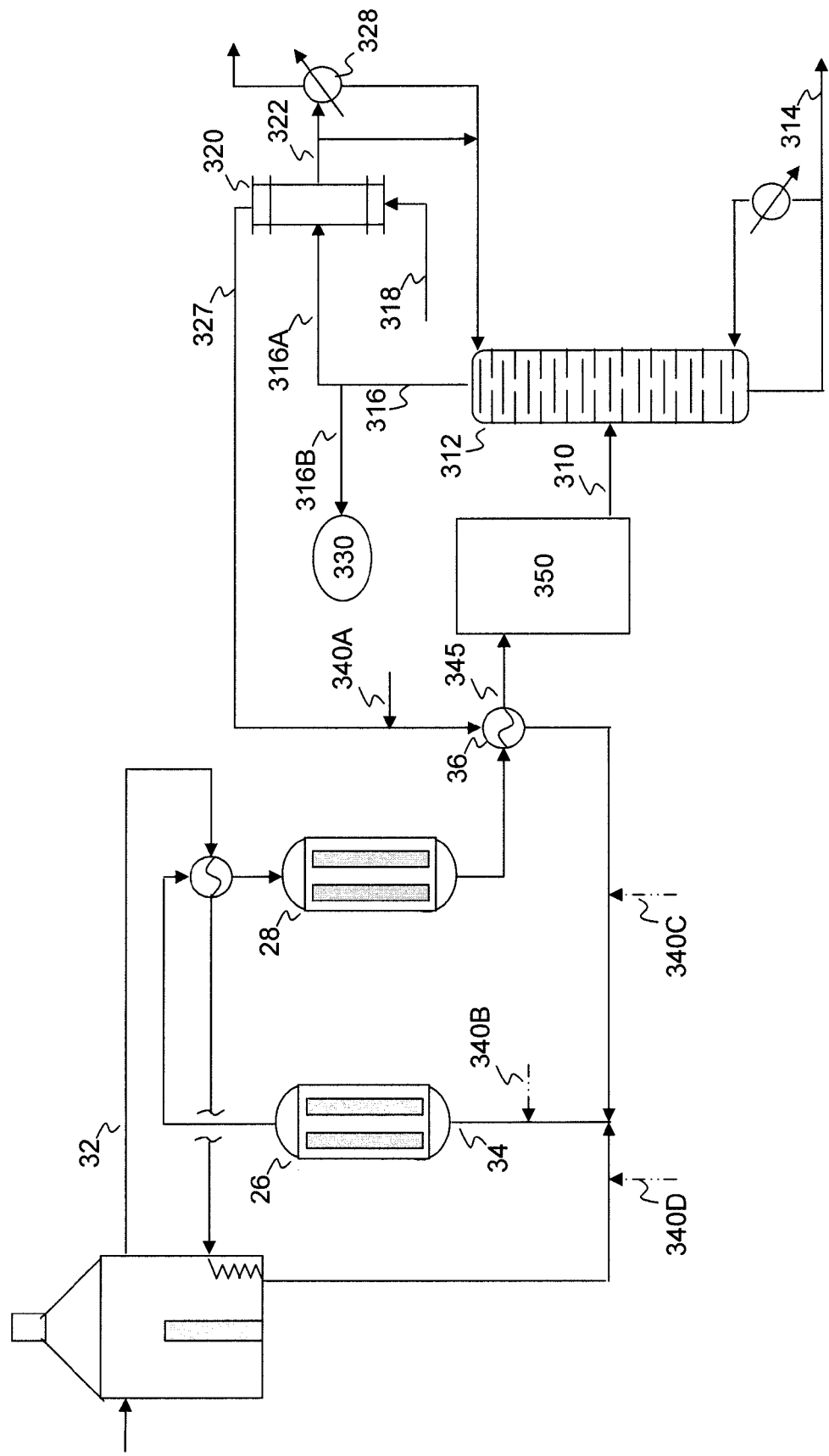
FIG. 4 is a simplified flow diagram of a portion of a process for the production of styrene monomer (SM) according to embodiments disclosed herein.

Referring now to FIG. 4, a simplified flow diagram of a process for the production of styrene monomer (SM) according to embodiments disclosed herein, where like numerals represent like parts. Ethylbenzene may be processed in the dehydrogenation reaction zone similar to that as described with respect to FIG. 2, producing a reactor effluent 345 that may be separated in separation zone 350 to result in a crude styrene product. Crude styrene 310 is then processed as described with respect to FIG. 3, producing only a portion of the required ethylbenzene vapor feed in azeotropic vaporizer 320, which is recovered via flow line 327.

Separation zone 350 may include, for example, separation of steam from the hydrocarbon vapors by condensation, separation of light hydrocarbons (BTX) from the ethylbenzene and styrene, or other separation processes that are known to one skilled in the art. BTX separation may alternatively be performed downstream of splitter 312. Condensate recovered in separation zone 350 may be combined with ethylbenzene to form the ethylbenzene-water mixture fed to the azeotropic vaporizer 320 via flow line 318.

The azeotropic mixture of ethylbenzene and steam in flow line 327 has a first steam to oil weight ratio (e.g., steam to ethylbenzene weight ratio or the weight ratio of steam to ethylbenzene plus other hydrocarbons, as may be appropriate). The specific steam to ethylbenzene weight ratio of the resulting azeotropic mixture may depend upon the temperature and pressure of the vaporization system. The steam to ethylbenzene weight ratio may be in the range from about 0.4 to about 0.6 in some embodiments, such as from a lower limit of 0.40, 0.42, 0.44, 0.45, 0.46, 0.47, 0.48, or 0.49 to an upper limit of 0.50, 0.51, 0.52, 0.53, 0.54, 0.55, 0.56, 0.58, or 0.60, where any lower limit may be combined with any upper limit.

The azeotropic mixture of ethylbenzene and steam in flow line 327 may then be combined with additional ethylbenzene and additional steam (such as the main steam) to result in the desired overall steam to oil weight ratio of the feed entering the dehydration reactor train at inlet 34. Ethylbenzene liquid and/or vapor may be added to the system via one or more of flow lines 340A, 340B, 340C, and 340D, or at other locations as may be envisioned by one skilled in the art. Where ethylbenzene liquid is fed to the system, it should be vaporized prior to being fed to reactors 26, such as by admixture with the main steam or via indirect heat exchange, such as with low pressure steam or in effluent exchanger 36, for example. The resulting overall steam to oil weight ratio of the feed entering the dehydration reactor used may depend upon the dehydrogenation catalyst type, catalyst age, or any number of other factors, and may be in the range from about 0.7 to about 1.5, by weight, for example. In other embodiments, the overall steam to oil ratio may be in the range from about 0.8 to about 1.2; from about 0.9 to about 1.0 in other embodiments; and in other embodiments from a lower limit of 0.70, 0.75, 0.80, 0.85, 0.90, 0.95, 1.0, 1.05, or 1.10 to an upper limit of 0.90, 0.95, 1.0, 1.05, 1.10, 1.15, 1.20, 1.25, 1.3, 1.35, 1.4, 1.45, or 1.50, where any lower limit may be combined with any higher upper limit In some embodiments, the azeotropic vaporization product in line 24 is combined with ethylbenzene vapor fed via flow line 340A. Following admixture of the additional ethylbenzene with the azeotropic mixture of ethylbenzene and steam, the resulting ethylbenzene-steam mixture may have a steam to oil weight ratio in the range from about 0.1 to about 0.5, such as from about 0.25 to about 0.35. In other embodiments, the resulting ethylbenzene-steam mixture may have a steam to oil weight ratio in the range from a lower limit of 0.10, 0.15, 0.20, 0.25, 0.30, or 0.35 to an upper limit of 0.20, 0.25, 0.30, 0.35, 0.40, 0.45, or 0.50, where any lower limit may be combined with any higher upper limit.

Referring again to FIG. 3, in some embodiments, portion 316B may bypass azeotropic vaporizer 320 and be condensed using cooling water or other cooling mediums, as may be available. For example, portion 316B may be fed to condenser 328, where it is condensed and recovered for use as reflux or feed to downstream processes. While excess heat from portion 316B may be lost to cooling water in this embodiment, this embodiment allows for the desired process flexibility to operate at lower overall steam to oil weight ratios while realizing some heat recovery in the azeotropic vaporizer.

Figure 5:
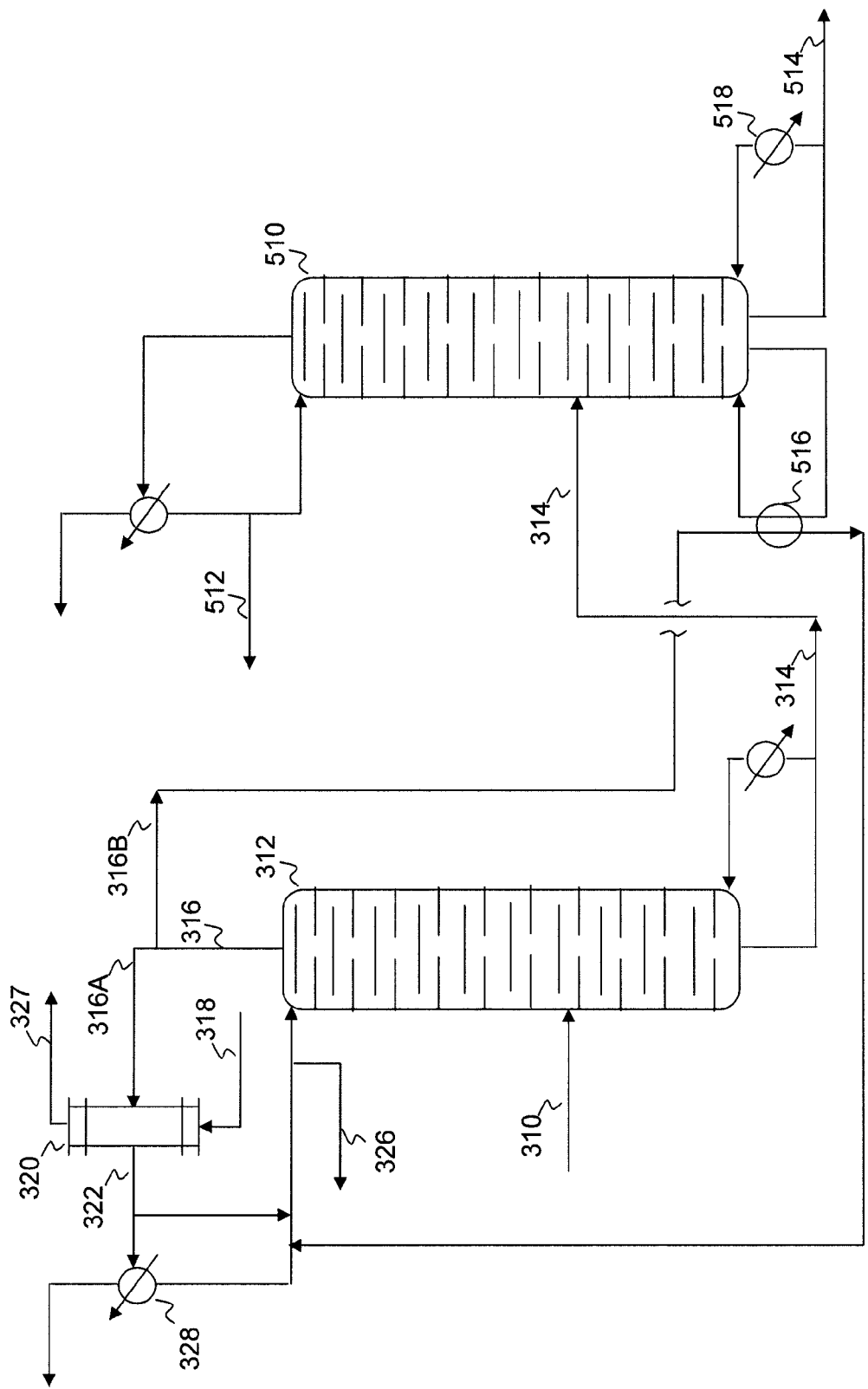
FIG. 5 is a simplified flow diagram of a portion of a process for the production of styrene monomer (SM) according to embodiments disclosed herein.

In other embodiments, heat may be recovered from portion 316B via indirect heat exchange with one or more suitable process streams in indirect heat exchange zone 330. For example, as illustrated in FIG. 5, where like numerals represent like parts, the bottoms fraction 314 from splitter 312 may be fed to a styrene recovery column 510 for separation of styrene from heavy reaction byproducts, such as oligomers, polymers, tars, and the like. The styrene may be recovered from column 510 as an overhead fraction via flow line 512, and the heavy byproducts may be recovered as bottoms fraction 514. Reboil vapor may be provided to styrene recovery column via indirect heat exchange with the portion 316B in heat exchanger 516. If necessary, a supplemental or startup reboiler 518 may be used to provide additional heat during normal operations or for startup of the column. In this manner, the overhead heat from the EB/SM splitter 312 may be efficiently utilized while reducing the primary steam to oil weight ratio, enabling the dehydrogenation reaction zone to operate at lower overall steam to oil weight ratios without facing any metallurgical limits for the steam superheater. In addition, as the overall steam to oil weight ratio may be reduced to 0.9 to 1.0, as compared to 1.15 or higher for prior art processes, the overall energy requirements for the production of styrene from ethylbenzene may be reduced.

As described above, embodiments disclosed herein may allow for the dehydrogenation of ethylbenzene at lower overall steam to ethylbenzene weight ratios (lower overall steam to oil weight ratios) while also recovering heat from process streams via the azeotropic vaporization of a portion of the liquid ethylbenzene and water feeds to the dehydrogenation reactor. Advantageously, embodiments disclosed herein may provide for one or more of: operation at low overall steam to oil weight ratios, such as weight ratios in the range from about 0.9 to 1.0; recovery of heat from the EB/SM splitter overhead fraction; reboil of the SM recovery column using a portion of the EB/SM splitter overhead fraction; operation at lower overall steam to oil weight ratios within steam superheater design limits; and a reduction in the overall energy requirements for producing styrene, among other advantages.

While the above description may refer to ethylbenzene and styrene, one skilled in the art can readily appreciate that the processes disclosed herein may be applicable to processes for the dehydrogenation of other alkylaromatic hydrocarbons. Additionally, it is understood that certain equipment, such as valves, piping, indicators, controls, optional equipment such as pumps, and the like have been omitted from the drawings to facilitate the description thereof, and that the placement of such equipment at appropriate places is deemed to be within the scope of one skilled in the art.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A process for the dehydrogenation of an alkylaromatic hydrocarbon, the process comprising:
   contacting a reactant vapor stream, comprising an alkylaromatic hydrocarbon and steam and having a first steam to alkylaromatic hydrocarbon weight ratio, with a dehydrogenation catalyst in a reaction zone comprising one or more reactors under dehydrogenation conditions so as to form a vapor phase effluent comprising a product hydrocarbon, the steam, and unreacted alkylaromatic hydrocarbon;
   feeding at least a portion of the effluent to a splitter to separate the product hydrocarbon from the unreacted alkylaromatic hydrocarbon;
   recovering the unreacted alkylaromatic hydrocarbon from the splitter as an overheads fraction;
   recovering the product hydrocarbon from the splitter as a bottoms fraction;
   recovering heat from a first portion of said overheads fraction by indirect heat exchange with a mixture comprising alkylaromatic hydrocarbon and water to at least partially condense said portion and to form an azeotropic vaporization product comprising alkylaromatic vapor and steam and having a second steam to alkylaromatic hydrocarbon weight ratio;
   combining the azeotropic vaporization product with additional alkylaromatic hydrocarbon to form a mixture having a third steam to alkylaromatic hydrocarbon weight ratio; and
   combining the mixture having a third alkylaromatic steam to alkylaromatic hydrocarbon weight ratio with additional steam to form the reactant vapor stream;
   wherein the first steam to alkylaromatic hydrocarbon weight ratio is in the range from about 0.7 to about 1.5, the second steam to alkylaromatic hydrocarbon weight ratio is in the range from about 0.4 to 0.6, and the third steam to alkylaromatic hydrocarbon weight ratio is in the range from about 0.1 to 0.5.

2. The process according to claim 1, further comprising:
   recovering heat from a second portion of the overheads fraction by indirect heat exchange.

3. The process according to claim 1, wherein the effluent further comprises reaction byproducts heavier than the product hydrocarbon, the process further comprising:

feeding the bottoms fraction to a product hydrocarbon recovery column to separate the product hydrocarbon from the reaction byproducts;

providing reboil vapor to the product hydrocarbon recovery column via indirect heat exchange with a second portion of the overheads fraction.

4. The process of claim 1, wherein the alkylaromatic hydrocarbon is ethylbenzene and the product hydrocarbon is styrene.

5. The process of claim 1, wherein the second steam to alkylaromatic hydrocarbon weight ratio is in the range from about 0.45 to about 0.55.

6. The process of claim 1, wherein the first steam to alkylaromatic hydrocarbon weight ratio is in the range from about 0.8 to about 1.2.

7. The process of claim 1, wherein the first steam to alkylaromatic hydrocarbon weight ratio is in the range from about 0.9 to about 1.0.

8. The process of claim 1, wherein the third steam to alkylaromatic hydrocarbon weight ratio is in the range from about 0.25 to about 0.35.

\* \* \* \* \*